US012691159B2

(12) United States Patent (10) Patent No.: US 12,691,159 B2
Lee et al. (45) Date of Patent: Jul. 28, 2026

(54) COMPOSITION FOR TREATING HAIR LOSS OR PROMOTING HAIR GROWTH

(71) Applicants: Medicosbiotech, Inc, Seoul (KR); Korea Advanced Institute of Science and Technology, Daejeon (KR)

(72) Inventors: Sang Yup Lee, Daejeon (KR); Won Min Yoo, Seoul (KR); Sooncheol Kim, Seoul (KR); Hannah Chung, Daejeon (KR); Deok Hyun Na, Seoul (KR)

(73) Assignees: KOREA ADVANCED INSTITUTE OF SCIENCE AND TECHNOLOGY, Daejeon (KR); MEDICOSBIOTECH, INC, Seoul (KR)

( * ) Notice: Subject to any disclaimer, the term of this patent is extended or adjusted under 35 U.S.C. 154(b) by 1022 days.

(21) Appl. No.: 17/296,310

(22) PCT Filed: Nov. 21, 2019

(86) PCT No.: PCT/KR2019/016012
§ 371 (c)(1),
(2) Date: May 24, 2021

(87) PCT Pub. No.: WO2020/106075
PCT Pub. Date: May 28, 2020

(65) Prior Publication Data
US 2022/0040261 A1 Feb. 10, 2022

(30) Foreign Application Priority Data
Nov. 23, 2018 (KR) ........................ 10-2018-0146288

(51) Int. Cl.
*A61K 38/17* (2006.01)
*A61K 35/16* (2015.01)
*A61P 17/14* (2006.01)

(52) U.S. Cl.
CPC .......... *A61K 38/1767* (2013.01); *A61K 35/16* (2013.01); *A61P 17/14* (2018.01)

(58) Field of Classification Search
None
See application file for complete search history.

(56) References Cited

U.S. PATENT DOCUMENTS

| | | | |
|---|---|---|---|
| 9,782,438 B2 | 10/2017 | Lim | |
| 2008/0193386 A1 | 8/2008 | Yoo et al. | |
| 2012/0164196 A1 | 6/2012 | Velazques Pereda et al. | |
| 2016/0235889 A1 | 8/2016 | Pallotta et al. | |

FOREIGN PATENT DOCUMENTS

| | | | |
|---|---|---|---|
| CN | 1513565 | A | 7/2004 |
| CN | 102906107 | B | 5/2015 |
| CN | 107208106 | A | 9/2017 |
| JP | 48019943 | A | 6/1973 |
| JP | 02311410 | A | 12/1990 |
| JP | 2002212092 | A | 7/2002 |
| JP | 2008222671 | A | 9/2008 |
| KR | 100617644 | * | 9/2006 |
| KR | 100617644 | B | 9/2006 |
| KR | 101236526 | B1 | 2/2013 |
| KR | 101236526 | * | 3/2013 |
| KR | 101236526 | B | 3/2013 |
| KR | 101317420 | * | 10/2013 |
| KR | 101317420 | B1 | 10/2013 |
| KR | 1020140029674 | A | 3/2014 |
| KR | 1020170126601 | A | 11/2017 |
| WO | 2011011347 | A2 | 1/2011 |
| WO | 2013159101 | A1 | 10/2013 |
| WO | 2015048344 | A2 | 4/2015 |
| WO | 2016001624 | A1 | 1/2016 |
| WO | 2017042048 | A1 | 3/2017 |
| WO | 2020206074 | A1 | 5/2020 |

OTHER PUBLICATIONS

Kunz et al., Biomed Research International, vol. 2016.*
Yanagihara et al., 2008 "Effects of Sericin on Promoting Proliferation and Inhibiting Apoptosis of Mammalian Cells," Animal Cell Technology: Basic & Applied Aspects 15 (6 pages).
International Search Report from related International Application No. PCT/KR2019/016012, mailed Feb. 25, 2020 (4 pages).
Written Opinion from related International Application No. PCT/KR2019/016012, mailed Feb. 25, 2020 (4 pages).
Office Action issued on May 7, 2024 for the Chinese Patent Application 201980086221.6.
English Translation of Office Action issued on May 7, 2024 for the Chinese Patent Application 201980086221.6.
Search Report issued on Apr. 30, 2024 for the Chinese Patent Application 201980086221.6.
Liu, Q., et al., "Recombinant spider silk proteins for application in inguinal hernia repair", Hernia Abdominal Wall Surg, 2018, pp. 252-254, vol. 12, No. 4, Publisher: China Academic Journal Electronic Publishing House.
Liu, Q., et al., "Recombinant spider silk proteins for application in inguinal hernia repair", Hernia Abdominal Wall Surg, 2018, pp. 252-254, English Translation, vol. 12, No. 4, Publisher: Chinese Academic Journal Electronic Publishing House.
Tinoco, A., et al., "Proteins as Hair Styling Agents", Applied Sciences, 2021, https://doi.org/10.3390/app11094245, vol. 11, No. 4245, Publisher: MDPI.
Wang, J., et al., "Research on spider silk protein and its genetic engineering", Silk Monthly, 2008, pp. 53-55, Publisher: China Academic Journal Electronic Publishing House.

(Continued)

*Primary Examiner* — Michael V Meller
(74) *Attorney, Agent, or Firm* — HULTQUIST, PLLC; Steven J. Hultquist

(57) ABSTRACT

The present invention relates to a composition for treating hair loss or promoting hair growth which contains a silk protein, and plasma or serum components. According to the present invention, due to the synergistic effect of a silk protein and plasma or serum components, the effect of promoting hair growth and the effect of treating hair loss can be expected to be more efficient.

1 Claim, 1 Drawing Sheet
Specification includes a Sequence Listing.

(56) References Cited

OTHER PUBLICATIONS

Wang, J., et al., "Research on spider silk protein and its genetic engineering", Silk Monthly, 2008, pp. 53-55, English Translation, Publisher: Chinese Academic Journal Electronic Publishing House.

Yao, Y., et al., "A Study of Sericin Protein on Hair-Care", Journal of Textile Research, 2004, DOI:10.13475/j.fzxb.2004.01.002, vol. 25, No. 1, Publisher: China Academic Journal Electronic Publishing House.

Yao, Y., et al., "A Study of Sericin Protein on Hair-Care", Journal of Textile Research, 2004, DOI:10.13475/j.fzxb.2004.01.002, English Translation, vol. 25, No. 1, Publisher: China Academic Journal Electronic Publishing House.

EESR issued on Oct. 11, 2022 for counterpartEP Patent Application No. 19886811.9, Oct. 11, 2022.

Xu, M., et al., "Structure of a protein superfiber: Spider dragline silk", Proc. Natl. Acad. Sci. USA, vol. 87, pp. 7120-7124, 1990.

Office Action Issued in Chinese Patent Application No. 201980086221.6 on Nov. 29, 2023, English Translation.

Office Action Issued in Chinese Patent Application No. 201980086221.6 on Nov. 29, 2023.

Search Report Issued in Chinese Patent Application No. 201980086221.6 on Nov. 29, 2023.

Jichao, L., et al., "Silk fibroin collagen composite scaffold combined with platelet-rich plasma for repairing skin injury", Chinese Journal of Tissue Engineering Research, 2023, pp. 3971-3976, vol. 27, No. 25, Publisher: Electronic Publishing HouseChina Academic Journal.

Jichao, L., et al., "Silk fibroin collagen composite scaffold combined with platelet-rich plasma for repairing skin injury", Chinese Journal of Tissue Engineering Research, 2023, pp. 2971-3976, vol. 27, No. 23, Publisher: China Academic Journal Electronic Publishing House, English Translation.

Loo, Y., et al., "Self-Assembled Proteins and Peptides as Scaffolds for Tissue Regeneration", Advanded Healthcare Materials, 2015, pp. 2557-2586, vol. 4, Publisher: wileyonlinelibrary.com.

Zhao, L, et al., "Progress in research work with respect to application of silk protein in cosmetics", China Surfactant Detergent & Cosmetics, 2012, DOI:10.13218/J.CNKI.CSDC.2012.06.016, vol. 42, No. 6, Publisher: China Academic Journal Electronic Publishing House.

Zhao, L, et al., "Progress in research work with respect to application of silk protein in cosmetics", China Surfactant Detergent & Cosmetics, 2012, DOI:10.13218/j.cnki.csdc.2012.06.016, vol. 42, No. 6, Publisher: China Academic Journal Electronic Publishing House, English Translation.

Houdek, M.T., et al., "Collagen and Fractionated Platelet-Rich Plasma Scaffold for Dermall Regeneration", Experimental, 2016, pp. 1498-1506, vol. 137, No. 5, Publisher: www.PRSJournal.com.

Mintel, "Anti-Hairloss Conditioner", Product Description, Dec. 2015, http://www.gnpd.com, Publisher: Mintel.

Mintel, "Moisturizing and Fortification Cream", Product Description, 2016, http://www.gnpd.com, Publisher: Mintel.

Mintel, "Seaweed Hair Treatment", Product Description, 2017, http://www.gnpd.com, Publisher: Mintel.

* cited by examiner

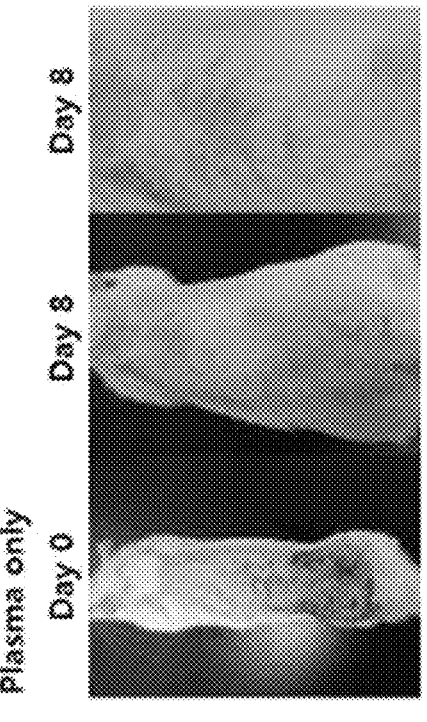
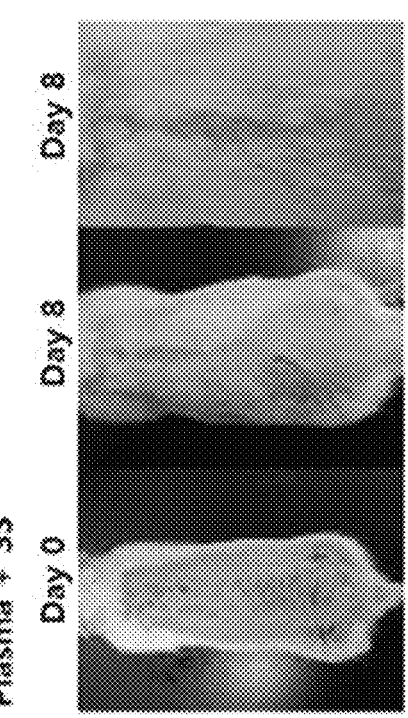
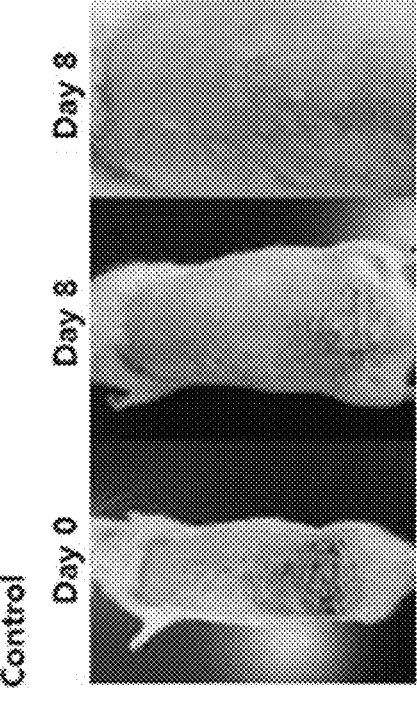
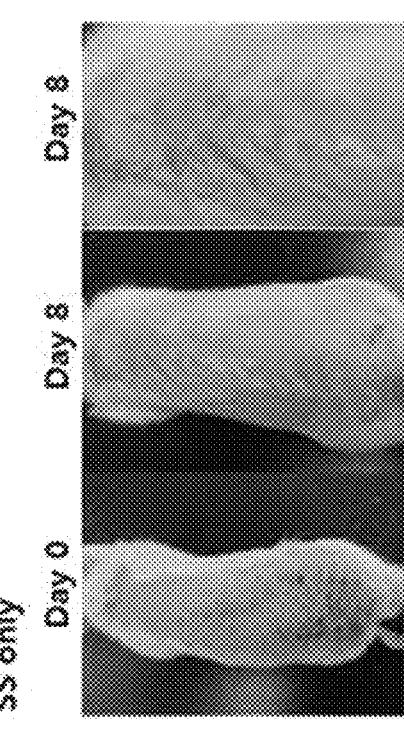

COMPOSITION FOR TREATING HAIR LOSS OR PROMOTING HAIR GROWTH

1. SEQUENCE LISTING

The application contains a Sequence Listing with has been submitted in ASCII format via EFS and is hereby incorporated by reference. The ASCII copy, created on May 7, 2021, is named PF_B2555_ST25.txt and is 1,224 bytes in size.

2. TECHNICAL FIELD

The present invention relates to a composition for treating hair loss or promoting hair growth comprising a silk protein and a plasma or serum component, and more specifically to a composition for treating hair loss or promoting hair growth comprising a silk protein having a molecular weight of 5 to 300 kDa, along with a plasma or serum component.

3. BACKGROUND

Hair loss is a problem that has plagued men and some women for a long time, and the most common type of hair loss in men is male pattern baldness or alopecia. In the case of general alopecia, hair loss occurs gradually over several years, begins most noticeably at the crown of the head, and proceeds to the frontal region. In the case of women suffering from alopecia, as the hair becomes thinner, hair loss occurs more uniformly than men's alopecia and often occurs after menopause. In order to alleviate or treat alopecia, efforts to develop substances for stimulating hair growth or reducing hair loss have continued for a long time in the cosmetic and pharmaceutical industries.

To date, a variety of compounds have been developed as candidates as a result of attempts to produce hair growth promoters. Publications including medical, scientific and patent literature disclose that various efforts have been made in treating and/or preventing hair loss and restoring and/or promoting hair growth, particularly with regard to hair on the human scalp. Indeed, many different active compounds have been proposed, and representative examples thereof include 2,4-diamino-6-piperidinopyrimidine-3-oxide (also known as "minoxidil"), and finasteride which is a specific inhibitor of type II reductase (U.S. Pat. Nos. 4,139,619 and 4,596,812). A drug that uses minoxidil as an active ingredient is commercially available under the trade name Rogaine (trademark of Pharmacia & Upjohn Company). Rogaine has been reported to reduce hair loss by up to 10% and promote hair growth in men suffering from male pattern baldness. Rogaine is a solution that is applied directly to the scalp area from the outside, and it is known that therapeutic application should be regularly sustained over a long period of time. Drugs using finasteride as an active ingredient are commercially available under the name Propecia (trademark of Merck & Co., Inc.). Propecia is a pill for oral administration. It also requires constant and regular administration.

Recently, it has been suggested that animal-derived serum or plasma has an effect of promoting hair growth (Korean Patent No. 0,617,644). Meanwhile, it has been suggested that many compositions based on natural plant extracts including medicinal herbs can be used for the treatment of alopecia. Various extracts of drugs commonly known as compositions for hair growth are used as hair growth stimulators or promoters. However, in practice, these extracts usually do not have a positive effect on hair growth because the condition of the hair or severity of alopecia varies from person to person. Although some compositions for hair growth are effective to some extent, they are accompanied by disadvantages including the difficulty in continuous use over a long period of time due to skin irritation and an unpleasant odor.

Another therapy for alopecia is hair transplantation. Typically, this method involves transplanting natural hair from a region of the scalp in which hair grows to the bald area. However, transplanted hair often falls out about 2 to 4 weeks after transplantation. Although most transplanted hair grows again after 3 to 4 months, additional transplant surgery may be required. Therefore, transplantation is expensive, time-consuming, painful and has a limited probability of success. Thus, there is an urgent need to develop methods and compositions for hair growth that exhibit excellent therapeutic effect for alopecia or an effect of promoting hair growth in a shorter period of time without causing side effects.

Accordingly, as a result of extensive efforts to develop a composition having an excellent therapeutic effect for hair loss and hair growth effect, the present inventors found that a composition comprising a silk protein along with a plasma or serum component derived from an animal has an effect of inducing and promoting hair growth in alopecia patients. Based on this finding, the present invention has been completed.

4. SUMMARY

It is one object of the present invention to provide a composition for promoting hair growth or inhibiting hair loss that has an effect of inducing and promoting hair growth in alopecia patients without causing side effects.

It is another object of the present invention to provide a method for treating or preventing alopecia comprising administering a blood plasma or serum component and a silk protein to a subject.

It is another object of the present invention to provide a method for promoting hair growth and inhibiting hair loss comprising administering a blood plasma or serum component and a silk protein to a subject.

It is another object of the present invention to provide the use of the blood plasma or serum component and the silk protein for promoting hair growth and inhibiting hair loss.

It is another object of the present invention to provide the use of the blood plasma or serum component and the silk protein for the preparation of a therapeutic agent for promoting hair growth and inhibiting hair loss.

To achieve the above object, the present invention provides a pharmaceutical composition for promoting hair growth and inhibiting hair loss comprising a blood plasma or serum component and a silk protein as active ingredients.

The present invention also provides a cosmetic composition for promoting hair growth and inhibiting hair loss comprising a blood plasma or serum component and a silk protein as active ingredients.

The present invention also provides a method for treating or preventing alopecia comprising administering a blood plasma or serum component and a silk protein to a subject.

The present invention also provides a method for promoting hair growth and inhibiting hair loss comprising administering a blood plasma or serum component and a silk protein to a subject.

The present invention also provides the use of the blood plasma or serum component and the silk protein for promoting hair growth and inhibiting hair loss.

The present invention also provides the use of the blood plasma or serum component and the silk protein for the preparation of a therapeutic agent for promoting hair growth and inhibiting hair loss.

5. BRIEF DESCRIPTION OF THE DRAWINGS

FIG. 1 shows the results of confirming the hair growth promotion effect of plasma and recombinant spider silk protein on depilated white mice.

6. DETAILED DESCRIPTION

Unless defined otherwise, all technical and scientific terms used herein have the same meanings as appreciated by those skilled in the field to which the present invention pertains. In general, the nomenclature used herein is well-known in the art and is ordinarily used.

In the present invention, it was confirmed that when a composition containing a human- or animal-derived blood plasma or serum component and a silk protein was applied to a depilated mouse, it exhibited an excellent hair growth effect, and that, when a shampoo containing a human- or animal-derived blood plasma or serum component and a silk protein was produced and applied to a hair loss patient, hair loss was inhibited and hair growth was promoted.

Accordingly, in one aspect, the present invention is directed to a pharmaceutical composition for promoting hair growth and inhibiting hair loss comprising a blood plasma or serum component and a silk protein as active ingredients.

In the present invention, the blood plasma or serum may be derived from humans or livestock.

In the present invention, the silk protein may be naturally derived, or may be a recombinant silk protein, and the silk protein may be a repeating peptide unit constituting a protein selected from the group consisting of dragline silk, elastin, silk fibroin, byssus, sericin, flagelliform silk, and collagen.

In the present invention, the silk protein may have a structure in which a repeating silk peptide unit having a glycine or serine content of 1% or more is repeated 1 to 160 times, and the silk protein may have a molecular weight of 5 to 300 kDa.

Silk proteins have been actively researched in recent years for various biochemical and pharmaceutical applications and thus are attracting attention as novel biomaterials. In the present invention, when silk proteins and silk peptides are contained in the composition for promoting hair growth and preventing hair loss based on the excellent moisturizing effect and superior adsorption to keratin thereof, there is an effect of making the hair rich.

The composition of the present invention may be prepared in a formulation selected from the group consisting of shampoos, creams, lotions, tonics, sprays, aerosols, oils, solutions, suspensions, gels, and ointments.

In another aspect, the present invention is directed to a cosmetic composition for promoting hair growth and inhibiting hair loss comprising a blood plasma or serum component and a silk protein as active ingredients.

In another aspect, the present invention is directed to the use of the blood plasma or serum for treating alopecia and/or promoting hair growth.

In another aspect, the present invention is directed to a method for treating or preventing alopecia comprising administering a blood plasma or serum component and a silk protein to a subject.

In another aspect, the present invention is directed to a method for promoting hair growth and inhibiting hair loss comprising administering a blood plasma or serum component and a silk protein to a subject.

In another aspect, the present invention is directed to the use of the blood plasma or serum component and silk protein for promoting hair growth and inhibiting hair loss.

In another aspect, the present invention is directed to the use of the blood plasma or serum component and silk protein for the preparation of a therapeutic agent for promoting hair growth and inhibiting hair loss.

The present invention is characterized by promoting, inducing and stimulating hair growth and/or reducing hair loss by topically applying a composition comprising blood plasma or serum as an active ingredient to a hair loss site of the scalp for about 1 to about 8 weeks.

As used herein, the term "hair loss inhibition" refers to preventing, inhibiting, blocking, or reducing partial or entire hair loss.

As used herein, the term "hair growth" is intended to encompass: the maintenance, induction, stimulation, promotion and regeneration of hair development in mammals; growth of defective hair; prolongation of the anagen (growing phase) in the pilar cycle; or conversion of vellus hair to terminal hair.

As used herein, the term "alopecia" refers to defective hair growth and partial or entire hair loss, and includes, but is not limited to, male hormonal alopecia or androgenic alopecia, toxic alopecia, alopecia areata, telogen alopecia, alopecia due to endocrine abnormalities, metabolic disorders and nutritional disorders, pharmaceutical alopecia, mechanical alopecia, alopecia due to skin diseases, scarring alopecia, congenital alopecia, and trichotillomania. Alopecia occurs when the pilar cycle breaks down. The most frequent phenomenon of alopecia is shortened hair growth or anagen (growing phase) due to the cessation of cell proliferation. This results from the early onset of catagen and ultimately causes a number of hairs to enter telogen. During telogen, the hair follicles detach from the dermal papilla and the hairs are lost. Alopecia has many etiologies including genetic factors, aging, local and systemic diseases, fever symptoms, mental stress, hormonal problems and side effects of drugs.

As used herein, the term "alopecia therapy (alopecia treatment)" refers to an action that prevents alopecia in animals capable of developing alopecia, and/or inhibits, delays or reduces alopecia, and/or promotes hair growth, and/or prolongs anagen (growing phase) in the pilar cycle, and/or converts vellus hair to terminal hair. Terminal hair is thick, colored, long hair with follicular roots implanted deeply in the dermis. Meanwhile, vellus hair is thin, smooth, short, bleached hair with the follicle roots located on the surface of the dermis. As alopecia progresses, hair changes from terminal hair to vellus hair.

The blood plasma used as an active ingredient in the present invention typically refers to a pale yellow liquid component from which tangible components in the blood of a mammal, that is, cells and cell fragments, are isolated, and the components and compositions thereof are well known (Philip Westerman, Plasma Proteins, VII-1 to VII-13, Sep. 17, 2002; and Wendy Y. Craig, et al., Plasma Proteins Pocket Guide, Foundation for Blood Research—the entire contents of which are incorporated herein by reference). Serum is also well defined, and is generally obtained by removing fibrinogen and other clotting factors from plasma.

The source of the blood plasma or serum in the present invention includes all species of mammals, including humans and non-human primates, for example, livestock including sheep, goats, pigs, horses, dogs, cattle, and other primates and rodents.

In the present invention, blood plasma or serum may be easily separated from the blood by well-known conventional methods, such as centrifugation, sedimentation (precipitation) or filtration. The centrifugation may be carried out under conditions suitable for sedimentation of blood cells from blood plasma. For example, the blood is centrifuged at about 3,000 rpm for about 10 minutes, which is sufficient to precipitate blood cells and leukocytes, as well as virtually all cell fragments including platelets.

The supernatant containing blood plasma can be easily separated from sedimented cells by standard techniques. The filtration may be performed by passing the blood through a filter suitable for separating blood cells from plasma. The filter may be a microporous membrane that enables proteins to easily penetrate the same.

Blood plasma or serum is known to be preserved in various forms before use, in addition to a fresh liquid plasma or liquid formulation obtained by centrifugation or sedimentation after blood collection. Examples of such forms include fresh frozen formulations, freeze-precipitated formulations, lyophilized formulations, concentrated formulations and the like. In the present invention, any type of blood plasma or serum as described above may be used. Fresh frozen plasma is prepared by centrifugation at about 2,800 rpm for about 15 minutes within 6 hours after blood collection to separate plasma from blood cells and freezing the same at a temperature of about −18° C. to −40° C. It is used after being thawed in hot water of 30 to 37° C.

Freeze-precipitated (cryoprecipitated) plasma is obtained by thawing one unit of fresh frozen plasma at about 4° C., separating the resultant white precipitate (cold precipitated protein containing large amounts of factors such as VIII:C, fibrinogen, XIII and fibronectin), and freezing the residue again at a temperature of −18 to −40° C. The freeze-precipitated formulation may be thawed by being placed in a refrigerator at 1 to 6° C. overnight, or may be thawed faster in a water bath at about 4° C. The concentrated plasma may be obtained by separating plasma from the blood, mixing the separated plasma with a concentrating agent such as dextranomer, Sephadex, dextramin, polyacrylamide, bio-gel P, silica gel, zeolite, Debrisan, cross-linked agarose, starch or alginate gel, and then separating the concentrating agent from the concentrated product.

In one embodiment of the present invention, the plasma or serum may be selected from commercially available products. For example, the plasma or serum may be selected from powder formulations commercially available by the blood bank, liquid formulations (e.g., Gibco™ Chicken Serum, Gibco™ Goat Serum, Gibco™ Lamb Serum, Gibco™ Porcine Serum, Gibco™ Rabbit Serum) produced by Invitrogen Corporation, and serum formulations (e.g., Chicken Serum (Cat. #100-161), Dog Serum (Cat. #100-160), Donor Donkey Serum (Cat. #100-151), Donor Goat Serum (Cat. #100-109), Donor Rat Serum (Cat. #100-155), Feline Serum (Cat. 100-153), Guinea Pig Serum (Cat. #100-130), Monkey Serum (Cat. #100-154), Mouse Serum (Cat. #100-113), Porcine Serum (Cat. #100-115), Rabbit Serum (Cat. #100-116), Rat Serum (Cat. #100-150), and Sheep Serum (Cat. #100-117)) produced by Gemini BioProducts, Inc. (CA 95776, USA). These products are derived from plasma units originated from animals including humans, and are identified to be non-reactive to several antigens and antibodies, such as hepatitis B surface antigen (HBsAg) and hepatitis C (HCV) antibody, and to be negative to HIV-1 and HIV-2 antibodies based on the results of testing. All plasma units used to prepare these formulations have been previously verified to be non-pathogenic. To reduce the risk of latent propagation of pathogens, the formulation may be treated with an organic solvent/detergent mixture such as tri(n-butyl)/phosphate/polysorbate 80, designed to inactivate enveloped viruses such as HIV, hepatitis B virus and HCV. In addition, efficiency of removal of the viruses may be enhanced by further performing nanofiltration.

In a further embodiment, the formulations are prepared using independent (and thus optional) purification (i.e., nanofiltration with a solvent detergent) or pasteurization. The purification may be carried out in a blood or plasma state.

The resulting plasma or serum fraction may be powderized by heating, lyophilization or another suitable drying method. For example, the plasma or serum may be lyophilized at a temperature below −40° C. for several days (e.g., about 7 days). Conventional methods and parameters known to those skilled in the art may be used.

In order to effectively treat alopecia or effectively promote hair growth, the activity of plasma or serum used in the method and pharmaceutical composition of the present invention should be facilitated on the target site. For this purpose, the composition suitable for use according to the present invention includes a formulation comprising plasma or serum as an active ingredient of the present invention in combination with a pharmaceutically acceptable carrier. The plasma or serum may be present in an amount of 0.001% to 99.999% based on the weight of the composition. As another method, the plasma or serum may be used as a formulation without a carrier. As used herein, the term "pharmaceutically acceptable" refers to a state in which an ingredient is miscible with other ingredients of a formulation and does not harm the recipient (patient).

In the present invention, the composition preferably comprises 0.01 to 10% of the blood plasma component and 0.001 to 10% of the silk protein, more preferably 0.1 to 2% of the blood plasma component and 0.01 to 1% of the silk protein, and even more preferably 0.2 to 1% of the blood plasma component and 0.02 to 0.1% of the silk protein.

When the composition contains the blood plasma in an amount of 10% or more, an improvement in the hair loss treatment effect cannot be expected in proportion to the amount of the blood plasma that is added, and when the composition contains the blood plasma in an amount of less than 0.01%, a hair loss treatment effect cannot be expected. When the composition contains the silk protein in an amount of 10% or more, an improvement in the hair loss treatment effect cannot be expected in proportion to the amount of the silk protein that is added, and when the composition contains the silk protein in an amount of less than 0.001%, the hair loss treatment effect cannot be expected.

The plasma or serum according to the present invention is typically administered in a topical form. Formulations suitable for topical administration include liquid or semi-liquid preparations such as lotions, emulsions, creams, ointments, liniments, sprays, aerosols, oils, pastes, gels, tonics, solutions or suspensions. In order to prepare these hair growth preparations, various ingredients may be mixed and dissolved, or the resulting mixture may be kneaded and then formulated using any devices or methods commonly used or well known in the pharmaceutical and/or cosmetic fields [Reference: Remington's Pharmaceutical Science, 15th Edition, 1975, Mack Publishing Company, Easton, Pennsylvania 18042 (Chapter 87: Blaug, Seymour)]. Preferred formulations include gels, ointments, lotions, and creams.

In the case of ointments, the plasma or serum is, for example, suspended or dissolved in a mixture of one or more of the following components: mineral oil, paraffin, mineral oil, white vaseline, propylene glycol, polyoxyethylene, polyoxypropylene, glycerin, stearyl alcohol, an emulsifying wax, cetanol, sodium lauryl sulfate, ethyl or butyl paraoxybenzoate, brine, and water. In the case of lotions or creams, the plasma or serum is, for example, suspended or dissolved in a mixture of one or more of the following components: mineral oil, sorbitan monostearate, polysorbate 60, vaseline, lanolin, saline, cetyl ester wax, cetearyl alcohol, 2-octyldodecanol, benzyl alcohol and water. In addition to the ingredients described above, the formulation of the present invention may further comprise one or more additional ingredients such as diluents, buffers, flavors, binders, surfactants, thickeners, lubricants, preservatives, pH adjusters, fungicides, antioxidants, emulsifiers, stabilizers, spices and colorants.

The dose of plasma or serum according to the present invention should be appropriately determined in consideration of gender, age, alopecia symptoms and hair condition. Typically, the plasma or serum is applied to the scalp in a daily single dose of about 0.1 to about 5 $mg/cm^2$ for an adult.

Hereinafter, the present invention will be described in more detail with reference to examples. However, it will be obvious to those skilled in the art that these examples are provided only for illustration of the present invention and should not be construed as limiting the scope of the present invention.

7. EXAMPLES

Example 1: Preparation of Ointment Containing Bovine Plasma and Serum 500 ml of fetal bovine serum (FBS; Biofluids. Inc, Rockville, MD) was charged in a vial for lyophilizing and was frozen in a freezer (Forma Scientific, Inc. Ohio, USA) at −80° C. for 6 hours. At this time, the FBS that is used had an endotoxin content of 0.1 ng/ml or less and a hemoglobin content of 30 ng/100 ml or less. The vial containing frozen FBS was mounted on a lyophilizing/shell freezing system (Labconco, Co. Kansas City, Missouri. USA), the system was operated, and lyophilizing was performed at −48° C. for 7 days to prepare a powder. At this time, all of the processes were performed under sterile conditions.

5 g of the powder prepared above was mixed with 95 g of a semi-base cream (Sam-A Pharmaceutical Co. Ltd.), after which an appropriate amount of physiological saline was added thereto and mixed, and IN HCl (hydrochloric acid) or IN NaOH (sodium hydroxide) was added thereto while stirring. The pH was measured with a pH meter (Orion) to prepare an ointment having a pH adjusted to 5.5.

Example 2: Preparation of Gel Containing Bovine Plasma or Serum and Silk Protein 5 parts by weight of the powder prepared in Example 1 was mixed with 95 parts by weight of components (including 38 mg of Carbopol ETD 2020, 116 mg of glycerin, 38 mg of propylene glycol, 192 mg of triethanolamine and an appropriate amount of purified water) to obtain a clear gel having a pH of 5.8 to 6.0. Carbopol ETD 2020 is an acrylate having a C10-C30 alkyl acrylate crosspolymer.

The recombinant silk protein was prepared according to the method described in a prior patent (Korean Patent No. 10-1317420 B1).

A high-molecular-weight recombinant silk or silk-like protein having a structure in which the peptide having the following sequence of SEQ ID NO: 1 is repeated 48 times was used.

8

SEQ ID NO: 1:
NH2-SGRGGLGGQGAGMAAAAAMGGAGQGGYGGLGSQGT-COOH

For production, fed-batch fermentation was performed, and the target protein was extracted using dialysis.

An essence containing 2.5% (25 g/L) of plasma and serum, and 4 g/L of the recombinant silk protein were dissolved in 80 ml of 1×PBS buffer to prepare a 5% stock, and the stock was diluted to adjust a final concentration to 0.05% to prepare a gel.

Example 3: Comparison of Hair Growth Promotion Effect of Bovine Plasma and Serum, and Recombinant Silk Protein To completely depilate the back area of eight 5-week-old white mice (400-500 g, Sprague-Dawley species), the hair was removed via shaving and was then completely removed by applying 20 to 30 g of a hair removal cream (Veet) to each mouse and removing the hair removal cream after 5 minutes. 40 mg of testosterone and 2 g of the gel were applied to the depilated area of each mouse twice daily in the morning and evening for 3 weeks. After 3 weeks, four mice that undergone no hair growth were selected and were depilated repeatedly.

The hair loss sites of four experimental white mice were treated at 3 g/mouse/day with a control gel, a gel containing plasma (2.5%) (Plasma only), a gel containing only a recombinant spider silk protein (0.05%) (SS only), and a gel containing both plasma (2.5%) and a recombinant spider silk protein (0.05%) (Plasma+SS) for 1 week.

After 8 days, the experimental animals were observed. As a result, as can be seen from FIG. 1, hairs naturally grown in the area to which the gel containing both the plasma and recombinant spider silk protein was applied were remarkably thicker and more numerous than in the control group. In addition, the hairs grown in the areas to which the ointment containing only bovine plasma and the ointment containing only the silk protein were applied were found to be thinner and fewer in number than those in the area to which the ointment containing both the plasma and silk protein was applied.

Example 4: Comparison of Hair Growth Promotion Effect of Bovine Serum and Sericin Peptide The hair loss sites of four experimental white mice prepared in the same manner as in Example 3 were treated at 3 g/mouse/day with a control gel, a gel containing plasma and serum, a gel containing only sericin (Sigma-Aldrich), and a gel containing plasma, serum and sericin protein for 1 week.

After 8 days, the experimental animals were observed. As a result, hairs naturally grown in the area to which the gel containing plasma, serum and sericin protein was applied were remarkably thicker and more numerous than in the control group. In addition, the hairs grown in the areas to which the ointment containing only the bovine serum and the ointment containing only the silk protein were applied were found to be thinner and fewer in number than those in the area to which the ointment containing both the serum and the silk protein was applied.

Example 5: Preparation of Shampoo Containing Bovine Serum and Silk Protein for Detecting Anti-Hair Loss Effect 5 g of the bovine serum powder prepared in Example 2, 50 g of a recombinant spider silk protein, 150 g of Olivem® (Sodium PEG-7 olive oil Carboxylate) as a surfactant, 150 g of amino acid, 150 g of babassuamidopropyl betaine, 30 g of BeauPlex vitamin as an additive, 45 g of DL-panthenol, 24 g of phytic acid, 30 g of a propolis extract, 60 g of MultiEx Naturotics, and 6 g of citric acid were stirred in a stirrer at a speed of about 25 rpm to prepare 3,000 g of shampoo 1.

5 g of the bovine serum powder prepared in Example 2, 150 g of Olivem® (Sodium PEG-7 olive oil Carboxylate) as a surfactant, 150 g of amino acid, 150 g of babassuamidopropyl betaine, 30 g of BeauPlex vitamin as an additive, 45 g of DL-panthenol, 24 g of phytic acid, 30 g of a propolis extract, 60 g of MultiEx Naturotics, and 6 g of citric acid were stirred in a stirrer at a speed of about 25 rpm to prepare 3,000 g of shampoo 2.

50 g of a silk protein, 150 g of Olivem® (Sodium PEG-7 olive oil Carboxylate) as a surfactant, 150 g of amino acid, 150 g of babassuamidopropyl betaine, 30 g of BeauPlex The shampoos 1 to 3 and positive control shampoo (Ts shampoo, http://www.talmo.com) were each used for 80 subjects in total (20 subjects/group), and the 80 subjects consisted of 60 men and 20 women in their 20 s to 60 s, and included 10 subjects who had already undergone hair loss and 30 subjects who were undergoing hair loss. The subjects of each group used the corresponding shampoo once a day for 30 days.

As a result, the shampoo 1 containing bovine serum and silk protein exhibited remarkably excellent anti-hair loss and hair growth effects.

8. INDUSTRIAL APPLICABILITY

According to the present invention, better effects of promoting hair growth and treating hair loss can be expected through synergistic effect of the silk protein and plasma or serum components.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

```
                        SEQUENCE LISTING

<160> NUMBER OF SEQ ID NOS: 2

<210> SEQ ID NO 1
<211> LENGTH: 35
<212> TYPE: PRT
<213> ORGANISM: Artificial Sequence
<220> FEATURE:
<223> OTHER INFORMATION: spider silk peptide

<400> SEQUENCE: 1

Ser Gly Arg Gly Gly Leu Gly Gly Gln Gly Ala Gly Met Ala Ala Ala
1               5                   10                  15

Ala Ala Met Gly Gly Ala Gly Gln Gly Gly Tyr Gly Gly Leu Gly Ser
            20                  25                  30

Gln Gly Thr
        35

<210> SEQ ID NO 2
<211> LENGTH: 38
<212> TYPE: PRT
<213> ORGANISM: Artificial Sequence
<220> FEATURE:
<223> OTHER INFORMATION: sericin silk peptide

<400> SEQUENCE: 2

Ser Ser Thr Gly Ser Ser Ser Asn Thr Asp Ser Asn Ser Asn Ser Val
1               5                   10                  15

Gly Ser Ser Thr Ser Gly Gly Ser Ser Thr Tyr Gly Tyr Ser Ser Asn
            20                  25                  30

Ser Arg Asp Gly Ser Val
        35
``` vitamin as an additive, 45 g of DL-panthenol, 24 g of phytic acid, 30 g of a propolis extract, 60 g of MultiEx Naturotics, and 6 g of citric acid were stirred in a stirrer at a speed of about 25 rpm to prepare 3,000 g of shampoo 3.

What is claimed is:

1. An emulsion for promoting hair growth and inhibiting hair loss consisting essentially of (i) a blood plasma or serum component; and (ii) silk protein having a structure in which the silk peptide is represented by the amino acid sequence of SEQ ID NO: 1 which is repeated 16 to 96 times.

* * * * *